United States Patent
Marchetti (10) Patent No.: US 9,448,186 B2
(45) Date of Patent: Sep. 20, 2016

(54) SYSTEM AND METHOD FOR DETERMINING A CONCENTRATION OF GAS IN A CONFINED SPACE

(75) Inventor: John A. Marchetti, Ellabell, GA (US)

(73) Assignee: Gulfstream Aerospace Corporation, Savannah, GA (US)

( * ) Notice: Subject to any disclaimer, the term of this patent is extended or adjusted under 35 U.S.C. 154(b) by 790 days.

(21) Appl. No.: 13/314,992

(22) Filed: Dec. 8, 2011

(65) Prior Publication Data

US 2013/0147493 A1 Jun. 13, 2013

(51) Int. Cl.
*G01N 22/00* (2006.01)
*G01N 33/00* (2006.01)

(52) U.S. Cl.
CPC .......... *G01N 22/00* (2013.01); *G01N 33/0036* (2013.01)

(58) Field of Classification Search
CPC .................................................. G01N 33/0036
USPC .......................................................... 324/639
See application file for complete search history.

(56) References Cited

U.S. PATENT DOCUMENTS

| | | | | |
|---|---|---|---|---|
| 4,520,654 A | * | 6/1985 | Terhune | G01N 29/024 376/256 |
| 4,549,080 A | * | 10/1985 | Baskins | G01N 21/3504 250/338.1 |
| 4,637,729 A | * | 1/1987 | Schoch | G01N 21/8507 250/227.25 |
| 4,873,481 A | | 10/1989 | Nelson et al. | |
| 5,124,653 A | | 6/1992 | Andresen et al. | |
| 5,507,173 A | * | 4/1996 | Shearer | G01N 22/00 324/636 |
| 5,526,676 A | | 6/1996 | Solheim et al. | |
| 5,572,031 A | | 11/1996 | Cooper et al. | |
| 6,084,415 A | * | 7/2000 | Bååth | G01N 22/00 324/637 |
| 6,427,521 B2 | | 8/2002 | Jakkula et al. | |
| 6,819,252 B2 | * | 11/2004 | Johnston et al. | 340/630 |
| 7,269,991 B2 | * | 9/2007 | Hirsch et al. | 73/1.02 |
| 2004/0256560 A1 | | 12/2004 | Russell | |
| 2008/0006775 A1 | * | 1/2008 | Arno et al. | 250/338.5 |

(Continued)

FOREIGN PATENT DOCUMENTS

| CN | 2630846 Y | 8/2004 |
|---|---|---|
| CN | 1584567 A | 2/2005 |

(Continued)

OTHER PUBLICATIONS

The International Bureau of WIPO, Notification Concerning Transmittal of International Preliminary Report on Patentability for International Patent Appln. No. PCT/US2012/068199 mailed Jun. 19, 2014.

(Continued)

*Primary Examiner* — Jermele M Hollington
*Assistant Examiner* — Dustin Dickinson
(74) *Attorney, Agent, or Firm* — Lorenz & Kopf, LLP (LKGlobal)

(57) ABSTRACT

A system for determining a concentration of gas in a confined space includes a first frequency generator for generating a first RF signal. A first antenna transmits the first RF signal across the confined space and second antenna receives the first RF signal. First and second RF signal power detectors detect the power of the first RF signal both prior to and after transmission through the confined space. A first comparator circuit determines a concentration of oxygen in the confined space based on the power of the first RF signal prior to transmission through the confined space and the power of the first RF signal received by the second antenna.

13 Claims, 4 Drawing Sheets

(56) References Cited

U.S. PATENT DOCUMENTS

| | | | |
|---|---|---|---|
| 2008/0226505 A1* | 9/2008 | Willettt et al. | 422/98 |
| 2009/0120161 A1* | 5/2009 | Ishiguro et al. | 73/23.21 |
| 2010/0140478 A1 | 6/2010 | Wilson et al. | |
| 2010/0206042 A1 | 8/2010 | Johns et al. | |
| 2011/0074440 A1* | 3/2011 | Davenport et al. | 324/601 |

FOREIGN PATENT DOCUMENTS

| | | |
|---|---|---|
| DE | 10 2004 046 500 B4 | 1/2009 |
| DE | 102004046500 B4 | 1/2009 |
| JP | S607347 A | 1/1985 |

OTHER PUBLICATIONS

PCT Search Report and Written Opinion mailed Feb. 8, 2013 in PCT/US2012/068199.

State Intellectual Property Office of the People's Republic of China, Office Action in Chinese Patent Application No. 201280060599.7 mailed Dec. 31, 2015.

European Patent Office, Extended European Search Report in Application No. 12855581.0 dated Sep. 17, 2015.

Michael Thompson, et al., "Remote Determination of Oxygen and Water at Millimeter wave frequencies using fibre optic communications network," Analytica Chimica Acta 476 (2003) 25-32, Department of Instrumentation and Analytical Science, University of Manchester, United Kingdom, Oct. 18, 2002.

Toshitatsu Suzuki, et al., "O2 Concentration Characteristics at 60 GHz Band and Diagnosis of Temperature, Pressure, and Concentration," Astronomy, Atmospheric and Environmental Science Conference, International Conf. on Infrared and Millimeter Waves and 12th Conf. on Terahertz Electronics, Research Laboratory of Electronics, Massachusetts Institute of Technology, Cambridge, MA, 2003.

* cited by examiner

SYSTEM AND METHOD FOR DETERMINING A CONCENTRATION OF GAS IN A CONFINED SPACE

BACKGROUND OF THE INVENTION

1. Field of the Invention

The invention relates generally to determining a concentration of gas in space. More specifically, the invention relates to determining a concentration of oxygen in an space.

2. Description of the Related Art

The sensing of a gas, e.g., oxygen ($O_2$), in a confined space is important in a number of applications. For instance, in automotive applications, oxygen sensors are critical to electronic fuel injection and emission control systems. In aircraft, oxygen sensors are needed to determine a concentration of oxygen in a fuel tank.

These oxygen sensors are most often implemented with a zirconia ceramic ("zirconia") sensing element. The zirconia sensing element is often heated to temperatures around 700° F. The use of a zirconia sensing element heated to such a high temperature provides obvious hazards when implemented in a fuel tank, e.g., in an aircraft wing.

Furthermore, to increase safety of a fuel tank, an inerting system may be implemented. Some inerting systems operate by inserting an inert gas, such as nitrogen, into the fuel tank to bring the fuel to air ratio below the lower flammable limit. As such, it is beneficial to determine the concentration and/or amount of nitrogen and/or oxygen in the fuel tank.

Accordingly, it is desirable to provide a sensing system for measuring a concentration of oxygen in a confined space. It is also desirable to provide a sensing system for measuring a concentration of nitrogen ($N^7$) in a confined space. Furthermore, other desirable features and characteristics of the present invention will become apparent from the subsequent detailed description of the invention and the appended claims, taken in conjunction with the accompanying drawings and this background of the invention.

BRIEF SUMMARY

A system for determining a concentration of gas in a confined space includes a first frequency generator for generating a first radio frequency (RF) signal. The system also includes a first antenna electrically connected to the first frequency generator for transmitting the first RF signal across the confined space. The system further includes a second antenna for receiving the first RF signal. A first RF signal power detector detects the power of the first RF signal prior to transmission through the confined space. A second RF signal power detector detects the power of the first RF signal received at the second antenna. The system further includes a first comparator circuit in communication with the first and second RF signal power detectors. The first comparator circuit determines a concentration of oxygen in the confined space based on at least the power of the first RF signal prior to transmission through the confined space and the power of the first RF signal received by the second antenna.

A method of determining a concentration of a gas in a confined space includes the step of generating a first RF signal. The first RF signal is transmitted from a first antenna across the confined space. The method further includes detecting the power of the first RF signal prior to transmission through the confined space. The method also includes the step of receiving the first RF signal at a second antenna. The power of the first RF signal received by the second antenna is determined. A concentration of oxygen in the confined space is determined based on at least the power of the first RF signal prior to transmission through the confined space and the power of the first RF signal received by the second antenna.

BRIEF DESCRIPTION OF THE DRAWINGS

Other advantages of the disclosed subject matter will be readily appreciated, as the same becomes better understood by reference to the following detailed description when considered in connection with the accompanying drawings wherein.

DETAILED DESCRIPTION

Referring to the FIGS., wherein like numerals indicate like parts throughout the several views, a system 10 and method for determining a concentration of a gas in a confined space 12 is shown and described herein.

Figure 1:
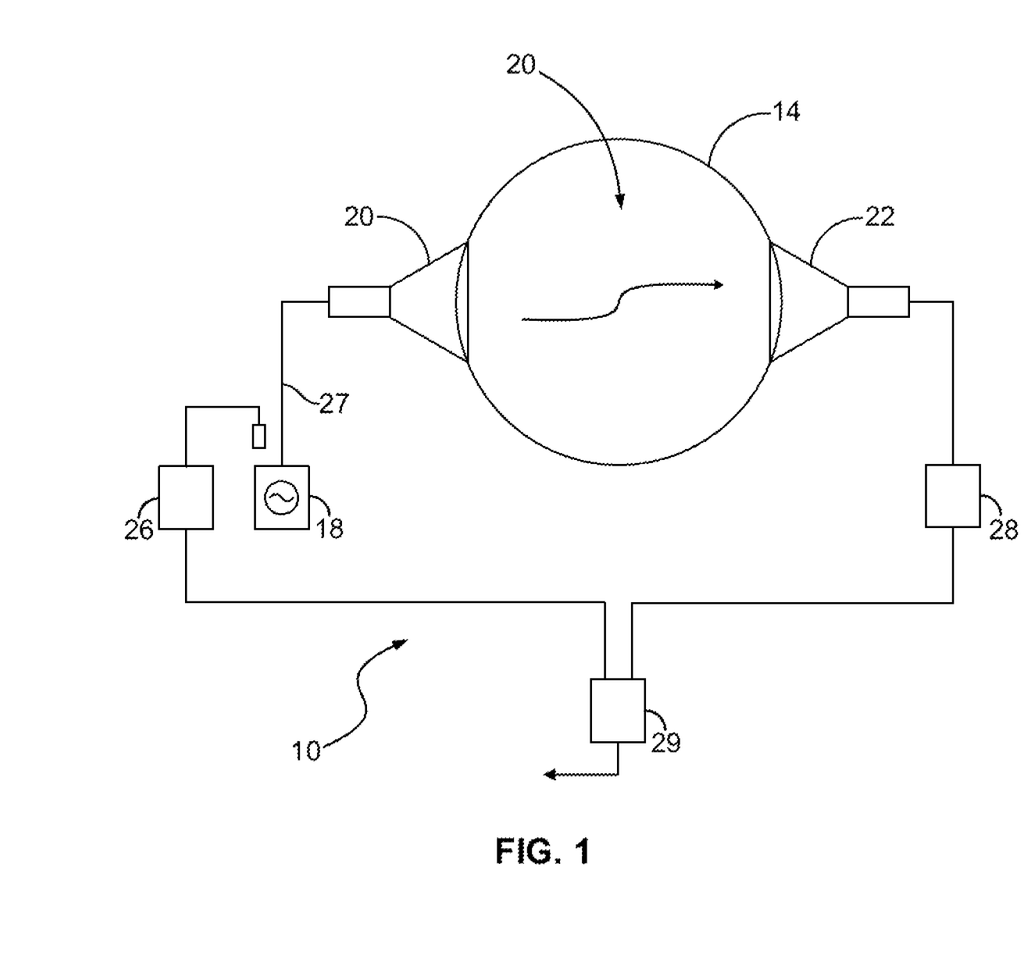
FIG. 1 is a schematic block diagram showing a cross-sectional representation of a confined space and a first embodiment of a system for determining a concentration of gas in that confined space.
Figure 2:
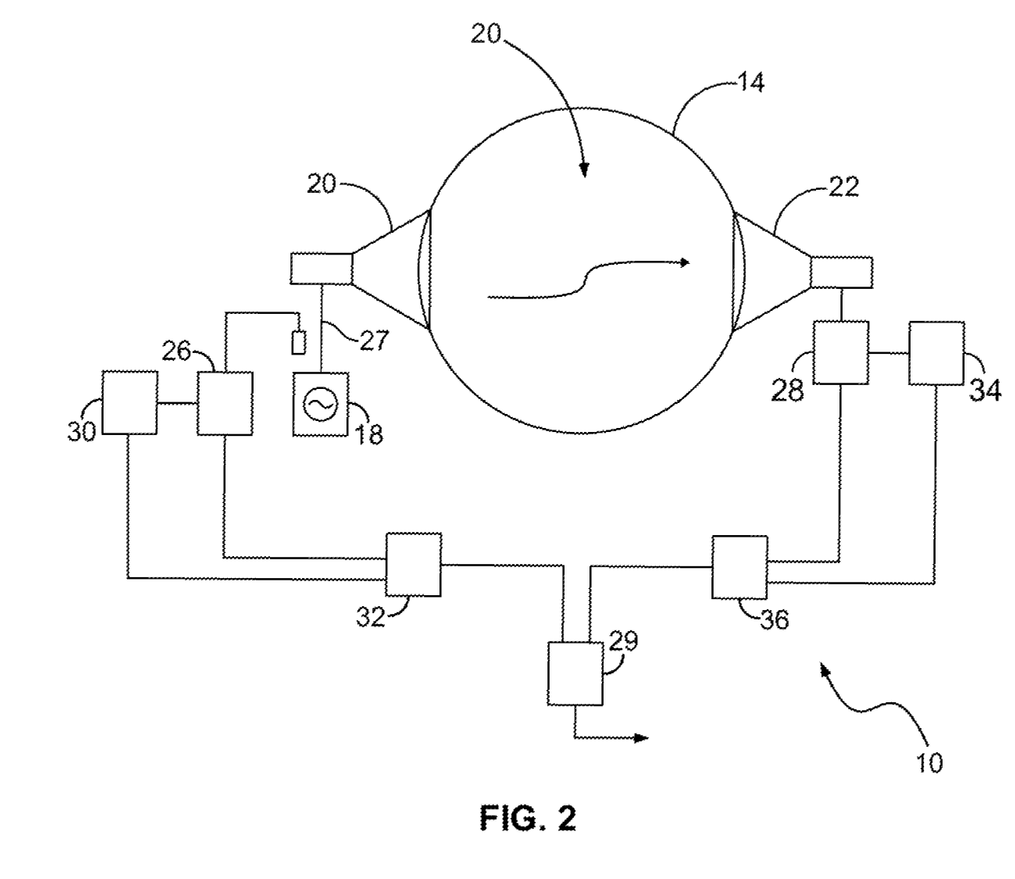
FIG. 2 is a schematic block diagram showing the cross-sectional representation of the confined space and a second embodiment of the system for determining a concentration of gas in that confined space.

The confined space 12 as described herein may be any volume that is partially or completely enclosed by a structure 14. For example, in a first embodiment and a second embodiment, as shown in FIGS. 1 and 2 respectively, the confined space 12 is a duct defined by a circular wall. In a third embodiment, as shown in FIG. 3, the confined space 12 is the interior of a fuel tank disposed in an aircraft wing 16.

Figure 3:
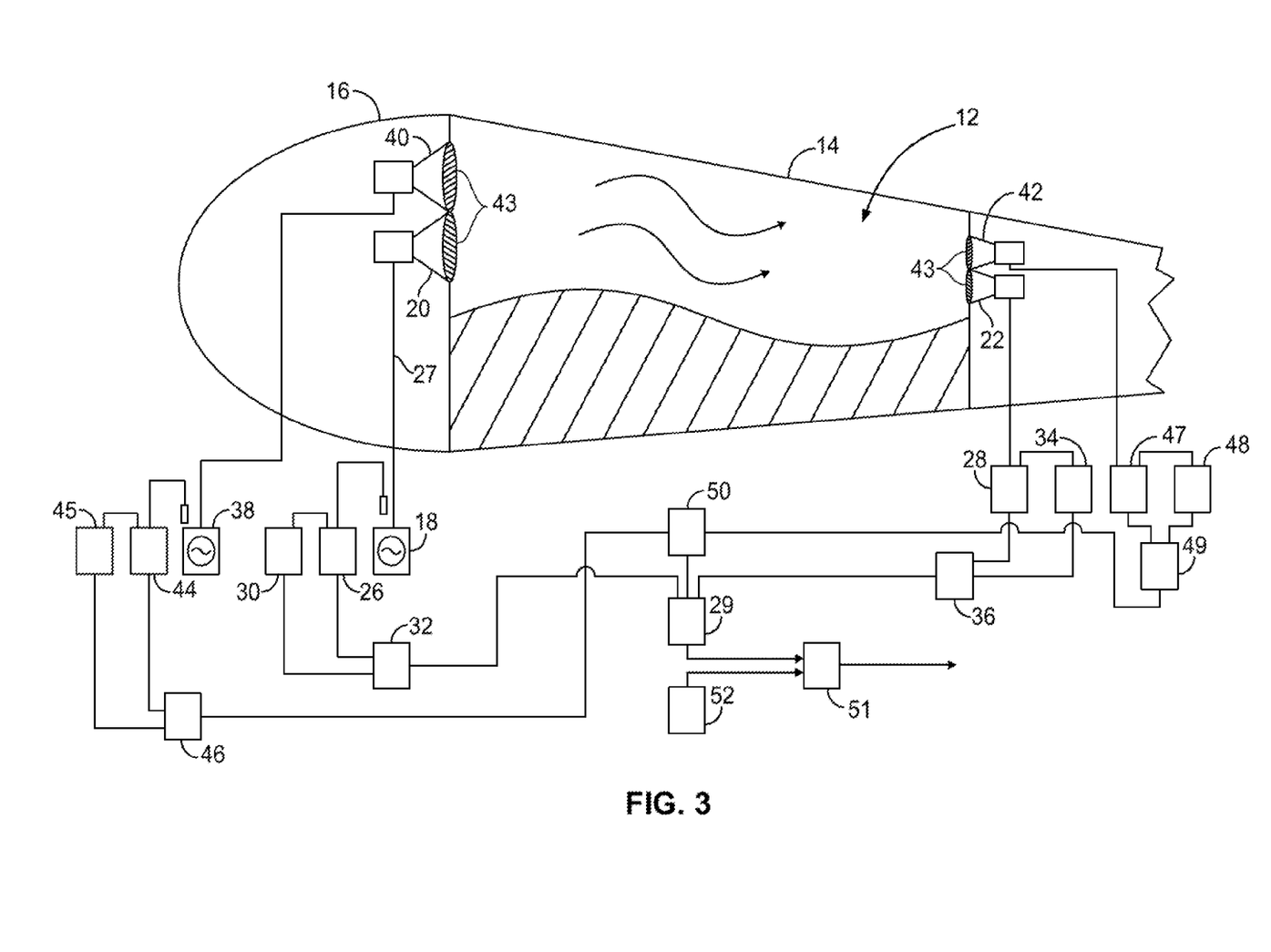
FIG. 3 is a schematic block diagram showing a cross-sectional representation of an aircraft wing with the confined space disposed therein and a third embodiment of the system for determining a concentration of gas in that confined space.
Figure 4:
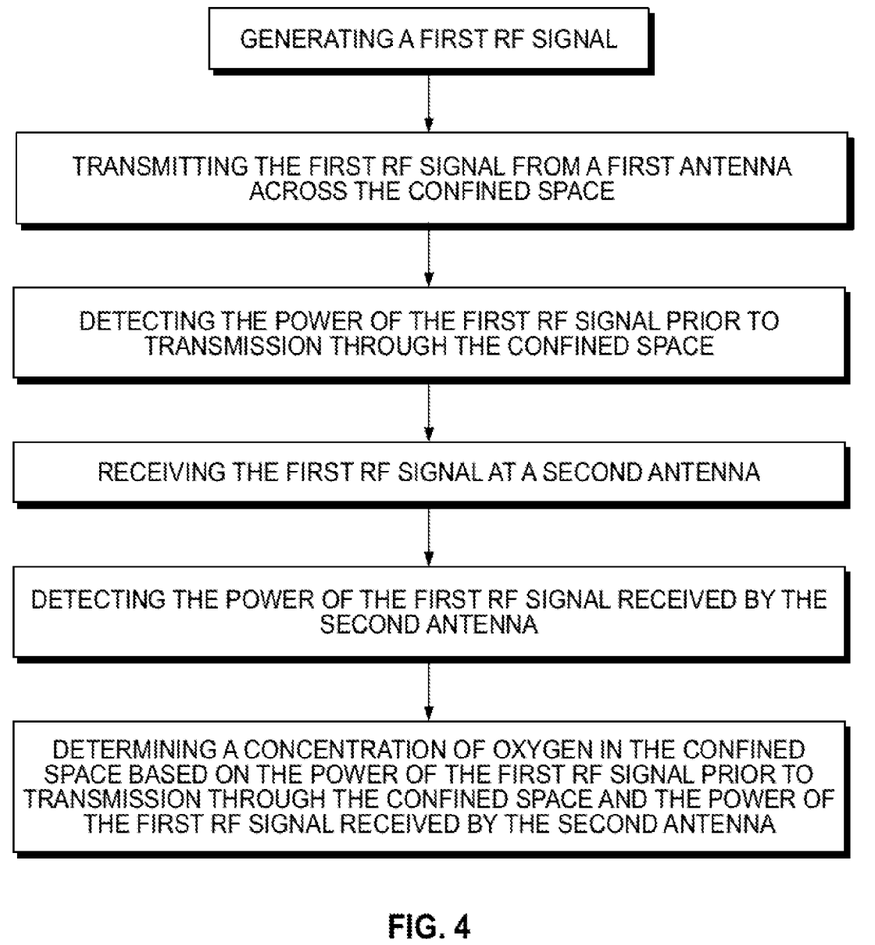
FIG. 4 is a flowchart showing the steps of a method of determining a concentration of gas in a confined space.

Referring to FIGS. 1 to 3, the system 10 includes a first frequency generator 18 for generating a first radio frequency (RF) signal. In the illustrated embodiments, the first RF signal generated by the first frequency generator 18 oscillates in the 60 GHz band. More specifically, the first RF signal oscillates at about 60.80 GHz.

A first antenna 20 (also commonly referred to as an "aerial") is electrically connected to the first frequency generator 18. The first antenna 20 receives the first RF signal from the first frequency generator 18 and transmits the first RF signal across the confined space 12. In the illustrated embodiments, the first antenna 20 is implemented as a horn antenna. That is, the first antenna 20 includes a waveguide (not shown) which flares in a horn shape to direct the first RF signal radio waves. However, other types and configurations of antennas may be suitable to implement the first antenna 20.

The system 10 also includes a second antenna 22 for receiving the first RF signal. The second antenna 22 of the illustrated embodiments is also implemented as a horn antenna. The second antenna 22 of the illustrated embodiments is disposed on an opposite side of the confined space 12 from the first antenna 20, such that the first RF signal passes through the confined space 12 between the first and second antennas 20, 22. The location and/or disposition of the first and second antennas 20, 22 may be varied depending on different implementations of the system 10.

RF signals in the 60 GHz band are subject to absorption by oxygen. Specifically, an attenuation of 16-18 dB per kilometer occurs in an RF signal near 60 GHz, above and beyond the attenuation caused by normal loss of the signal through the atmosphere, commonly referred to as the "free-space path loss". Even more specifically, the attenuation is 16 dB per kilometer at 20.9% pressure density. As such, the first RF signal being transmitted in the 60 GHz band will suffer a loss in signal strength due to the concentration of oxygen ($O_2$) in the confined space 12 and the free-space path loss. Said another way, the power of the first RF signal will be attenuated in proportion to the concentration of oxygen in the confined space 12 and the free-space path loss.

The system 10 may include a first RF signal power detector 26. The first RF signal power detector 26 detects the power of the first RF signal prior to transmission across the confined space 12. Specifically, the first RF signal power detector detects the power of the first RF signal generated by the first frequency generator 18 or the power of the first RF signal transmitted by the first antenna 20. In the illustrated embodiment, the first RF signal power detector 26, as shown in FIGS. 1-3, is electrically coupled to a feed line 27 that electrically connects the first RF generator 18 to the first antenna 20. The first RF signal power detector 26 may also generate a first power signal corresponding to the first RF signal. Also in the illustrated embodiments, the first RF signal power detector 26 is implemented as a stand-alone device. However, those skilled in the art realize that the first RF signal power detector 26 may be integrated with the first RF generator 18, the first antenna 20, or other suitable device.

The system 10 also may include a second RF signal power detector 28. The second RF signal power detector 28 detects the power of the first RF signal received by the second antenna 22 and generates a second power signal corresponding to the first RF signal. The second RF signal power detector 28 of the illustrated embodiments, as shown in FIGS. 1 to 3, is electrically connected to the second antenna 22. In the illustrated embodiments, the second RF signal power detector 28 is a stand-alone device. However, those skilled in the art realize that the second RF signal power detector 28 may be integrated with the second antenna 22 or other suitable device.

The system 10 further includes a first comparator circuit 29. The first comparator circuit 29 is utilized to determine a concentration of oxygen in the confined space 12 based on the attenuation of the first RF signal across the confined space 12. Preferably, the first comparator circuit 29 also takes in account the free-space path loss. In the illustrated embodiments, the first comparator circuit 29 receives signals corresponding generally to the power of the first RF signal transmitted by the first antenna 20 and the power of the first RF signal received by the second antenna 22. In the illustrated embodiments, as shown in FIGS. 1 to 3, the first comparator circuit 29 is in communication with the first and second RF signal power detectors 26, 28.

The first comparator circuit 29 may be implemented with an error summation amplifier circuit. This analog circuit receives the signals representing the first RF signals before and after transmission through the confined space 12 and produces a resultant signal representing the concentration of oxygen in the confined space 14. Alternatively, the first comparator circuit 29 may be implemented with a digital circuit, e.g., a microprocessor or other electronic computational device. Furthermore, those skilled in the art will realize other suitable techniques for implementing the first comparator circuit 29. The first comparator circuit 29 of the illustrated embodiments produces an output signal which encodes the concentration of oxygen in the confined space 12.

Referring to FIG. 2, the system 10 of the second embodiment further includes a first thermal reference device 30 for sensing a first temperature. More specifically, the first thermal reference device 30 senses the first temperature at or adjacent to the first RF signal power detector 26. In the illustrated embodiments, the first thermal reference device 30 is implemented with a Gallium Arsenide (GaAs) thermal detector. However, those skilled in the art will realize other suitable detectors to implement the first thermal reference device 30.

The system 10 of the second embodiment further includes a second comparator circuit 32 in communication with the first thermal reference device 30 and the first RF signal power detector 26. The second comparator circuit 32 receives the first power signal from the first RF signal power detector 26 and a first temperature signal from the first thermal reference device 30. The second comparator circuit 32 adjusts the first power signal to compensate for variations in the first temperature. The second comparator circuit 32 then provides a first temperature compensated RF signal. As such, the second comparator circuit 32 compensates for the temperature at the first antenna 20 and provides a first temperature compensated power signal.

Similar to the first comparator circuit 29, the second comparator circuit 32 may be implemented with an analog circuit, e.g., an error summation amplifier circuit, and/or a digital circuit, e.g., a microprocessor or other electronic computational device. Furthermore, those skilled in the art will realize other suitable techniques for implementing the second comparator circuit 32.

The system 10 of the second embodiment further includes a second thermal reference device 34 for sensing a second temperature. More specifically, the second thermal reference device 34 senses the second temperature at or adjacent to the second RF signal power detector 28. In the illustrated embodiments, the second thermal reference device 34 is implemented with a GaAs thermal detector. However, those skilled in the art will realize other suitable detectors to implement the second thermal reference device 34.

The system 10 of the second embodiment further includes a third comparator circuit 36 in communication with the second thermal reference device 34 and the second RF signal power detector 28. The third comparator circuit 34 receives the second power signal from the second RF signal power detector 28 and a second temperature signal from the second thermal reference device 34. The third comparator circuit 36 adjusts the second power signal to compensate for variations in the second temperature. The third comparator circuit 36 then provides a second temperature compensated RF signal. As such, the third comparator circuit 36 compensates for the temperature at the second antenna 22 and provides a second temperature compensated power signal.

Like the first comparator circuit 29, the third comparator circuit 34 may be implemented with an analog circuit, e.g., an error summation amplifier circuit, and/or a digital circuit, e.g., a microprocessor or other electronic computational device. Furthermore, those skilled in the art will realize other suitable techniques for implementing the third comparator circuit 34.

The first comparator circuit 29 of the second embodiment is in communication with the second and third comparator circuits 32, 36 and receives the first and second temperature compensated power signals. The first comparator circuit 29 determines the amount of oxygen in the confined space 12 based at least partially on the attenuation of the first RF signal across the confined space 12, as represented by the first and second power signals.

Referring now to FIG. 3, a third embodiment of the system 10 includes the first RF generator 18, the first antenna 20, the second antenna 22, the first RF signal power detector 24, the second RF signal power detector 28, the first thermal reference device 30, the second comparator circuit 32, the second thermal reference device 34, and the third comparator circuit 36 as described above with reference to the second embodiment.

The system 10 of the third embodiment further includes a second frequency generator 38 for generating a second RF signal. The second RF signal generated by the second frequency generator 38 oscillates in the 24 GHz band. A third antenna 40 is electrically connected to the second frequency generator 38. The third antenna 40 receives the second RF signal and transmits the second RF signal from the second frequency generator 38 across the confined space 12. In the third embodiment, the third antenna 40 is implemented as a horn antenna. That is, the third antenna 40 includes a waveguide (not shown) which flares in a horn shape to direct the second RF signal radio waves. However, other types and configurations of antennas may be suitable to implement the second antenna 40. Furthermore, the third antenna 40 may be integrated with the first antenna 20 or the second antenna 22, as will be appreciated by those skilled in the art.

The system 10 of the third embodiment also includes a fourth antenna 42 for receiving the second RF signal. The fourth antenna 42 is also implemented as a horn antenna and is disposed on an opposite side of the confined space 12 from the third antenna 42, such that the second RF signal passes through the confined space 12 between the third and fourth antennas 40, 42. Furthermore, the fourth antenna 42 may be integrated with the first antenna 20 or the second antenna 22, as will be appreciated by those skilled in the art. Moreover, the location and/or disposition of the third and fourth antennas 40, 42 may be varied depending on different implementations of the system 10.

The system 10 of the third embodiment may further include lenses 43 covering the horns of the antennas 20, 22, 40, 42. The lenses 43 provide a fuel-resistant barrier between the confined space 12, i.e., the fuel tank, and the antennas 20, 22, 40, 42 while allowing RF signal to pass therethrough. Furthermore, the lenses 43 may be used to focus the RF signal. The lenses 43 comprise an anti-corrosive dielectric material; however other materials may alternatively be used as appreciated by those skilled in the art.

RF signals in the 24 GHz band are subject to absorption by water vapor. As such, the second RF signal being transmitted in the 24 GHz band will suffer a loss in strength, i.e., an attenuation, based on the amount, i.e., concentration, of water vapor in the confined space 12.

The system 10 may include a third RF signal power detector 44. The third RF signal power detector 44 detects the power of the second RF signal prior to transmission across the confined space 12. Specifically, the second RF signal power detector detects the power of the first RF signal generated by the second frequency generator 38 or the power of the second RF signal transmitted by the third antenna 40. In the illustrated embodiment, the third RF signal power detector 44, as shown in FIG. 3, is electrically coupled to a feed line (not numbered) that electrically connects the second RF generator 38 to the third antenna 40. The third RF signal power detector 44 may also generate a third power signal corresponding to the second RF signal.

The system 10 of the third embodiment further includes a third thermal reference device 45 for sensing a third temperature. More specifically, the third thermal reference device 45 senses the third temperature at or adjacent to the third RF signal power detector 44. In the illustrated embodiments, the third thermal reference device 45 is implemented with a Gallium Arsenide (GaAs) thermal detector. However, those skilled in the art will realize other suitable detectors to implement the third thermal reference device 45.

The system 10 of the third embodiment includes a fourth comparator circuit 46 in communication with the third thermal reference device 45 and the third RF signal power detector 44. The fourth comparator circuit 46 receives the third power signal from the third RF signal power detector 44 and a third temperature signal from the third thermal reference device 45. The fourth comparator circuit 46 adjusts the third power signal to compensate for variations in the third temperature. The fourth comparator circuit 46 then provides a third temperature compensated signal.

The system 10 also may include a fourth RF signal power detector 47. The fourth RF signal power detector 47 detects the power of the second RF signal received by the fourth antenna 42 and generates a fourth power signal corresponding to the second RF signal. The fourth RF signal power detector 47 of the third embodiment, as shown in FIG. 3, is electrically connected to the fourth antenna 42. In the third embodiment, the fourth RF signal power detector 47 is a stand-alone device. However, those skilled in the art realize that the fourth RF signal power detector 47 may be integrated with the fourth antenna 42 or other suitable device.

The system 10 of the third embodiment further includes a fourth thermal reference device 48 for sensing a fourth temperature. More specifically, the fourth thermal reference device 48 senses the four temperature at or adjacent to the fourth RF signal power detector 47. In the illustrated embodiments, the fourth thermal reference device 48 is implemented with a GaAs thermal detector. However, those skilled in the art will realize other suitable detectors to implement the fourth thermal reference device 48.

The system 10 of the third embodiment further includes a fifth comparator circuit 49 in communication with the fourth thermal reference device 48 and the fourth RF signal power detector 47. The fifth comparator circuit 49 receives the fourth power signal from the fourth RF signal power detector 47 and a fourth temperature signal from the fourth thermal reference device 48. The fifth comparator circuit 49 adjusts the fourth power signal to compensate for variations in the fourth temperature. The fifth comparator circuit 49 then provides a fourth temperature compensated RF signal.

Water vapor increases the losses in millimeter wave signals, including those at 60 GHz. As such, it is helpful to subtract out the losses caused by the water vapor, in order to achieve an accurate estimate of oxygen in the confined space 12. This is particularly important in an aircraft wing 16 implementation of the confined space 12, which is subject to high humidity.

The system 10 of the third embodiment further includes a sixth comparator circuit 50 in communication with the second frequency generator 38 and the fourth antenna 42. More specifically, the sixth comparator circuit 50 is electrically connected to the fourth and fifth comparator circuits 46, 49. The sixth comparator circuit 50 determines an amount, i.e., a concentration, of water vapor in the confined space 12 based on temperature compensated signals corresponding to the second RF signal transmitted by the third antenna 40 and received by the fourth antenna 42.

Like the first comparator circuit 29, the sixth comparator circuit 50 may be implemented with an analog circuit, e.g., an error summation amplifier circuit, and/or a digital circuit, e.g., a microprocessor or other electronic computational device. Furthermore, those skilled in the art will realize other suitable techniques for implementing the sixth comparator circuit 50.

The first comparator circuit 29 of the third embodiment is in communication with the second, third, and sixth comparator circuits 32, 36, 50 and receives signals from these other comparator circuits 32, 36, 50. The first comparator circuit 29 determines the concentration of oxygen in the confined space 12 based on the attenuation of the first and second RF signals across the confined space 12. In computing the concentration of oxygen in confined space 12, the first comparator circuit 29 of the third embodiment compensates for the concentration of water vapor in the confined space 12, as provided by the sixth comparator circuit 50. The first comparator circuit 29 produces an output signal which encodes the concentration of oxygen in the confined space 12.

The system 10 of the third embodiment further includes a seventh comparator circuit 51. The seventh comparator circuit 51 is in communication with the first comparator circuit 29 for receiving the concentration of oxygen in the confined space 12. The seventh comparator circuit 51 is also in communication with an altimeter 52. The altimeter 52 provides a current altitude of the confined space 12, particularly when the confined space is part of the aircraft wing 16.

Like the first comparator circuit 29, the seventh comparator circuit 51 may be implemented with an analog circuit, e.g., an error summation amplifier circuit, and/or a digital circuit, e.g., a microprocessor or other electronic computational device. Furthermore, those skilled in the art will realize other suitable techniques for implementing the seventh comparator circuit 51.

By utilizing the concentration of oxygen in the confined space 12 and the altitude of the confined space 12, the fifth comparator circuit 46 determines an amount of nitrogen ($N^7$) in the confined space 12. Specifically, the nitrogen is derived as the nitrogen is the dominant element once the concentration of oxygen is subtracted out, as trace gases in the atmosphere typically account for less than 1%. By determining the amount of nitrogen in the confined space 12, an effective amount of nitrogen purge for wing tank inerting may be developed.

The present invention has been described herein in an illustrative manner, and it is to be understood that the terminology which has been used is intended to be in the nature of words of description rather than of limitation. Obviously, many modifications and variations of the invention are possible in light of the above teachings. The invention may be practiced otherwise than as specifically described within the scope of the appended claims.

What is claimed is:

1. A system for determining a concentration of gas in a confined space, said system comprising:
   a first frequency generator for generating a first radio frequency (RF) signal;
   a first antenna electrically connected to said first frequency generator for transmitting the first RF signal across the confined space;
   a second antenna for receiving the first RF signal;
   a first RF signal power detector for detecting the power of the first RF signal prior to transmission through the confined space and generating a first power signal corresponding to the first RF signal prior to transmission;
   a second RF signal power detector for detecting the power of the first RF signal received at said second antenna and generating a second power signal corresponding to the first RF signal received at said second antenna;
   a first comparator circuit in communication with said first and second RF signal power detectors for determining a concentration of oxygen in the confined space based on at least the first power signal and the second power signal;
   at least one thermal reference device for sensing a temperature;
   a temperature compensation comparator circuit in communication with said at least one thermal reference device, said first RF signal power detector for adjusting the first power signal to compensate for the temperature, and said second RF signal power detector for adjusting the second power signal to compensate for the temperature;
   a second frequency generator for generating a second RF signal;
   a third antenna electrically connected to said second frequency generator for transmitting the second RF signal across the confined space;
   a fourth antenna for receiving the RF signal; and
   a sixth comparator circuit in communication with said second frequency generator and said fourth antenna for determining a concentration of water vapor in the confined space based on at least the second RF signal prior to transmission through the confined space and the second RF signal received by said fourth antenna,
   wherein said first comparator circuit is in communication with said sixth comparator circuit for determining a concentration of water vapor in the confined space and determining a concentration of oxygen in the confined space based on at least the power signals corresponding to the first RF signal and the concentration of water vapor in the confined space.

2. A system as set forth in claim 1 wherein the first RF signal is in the 60 GHz frequency band.

3. A system as set forth in claim 1 wherein said at least one thermal reference device comprises a first thermal reference device for sensing a first temperature at or adjacent to said first RF signal power detector and a second thermal reference device for sensing a second temperature at or adjacent to said second RF signal power detector.

4. A system as set forth in claim 3 wherein said temperature compensation comparator circuit comprises a second comparator circuit in communication with said first thermal reference device and said first RF signal power detector for adjusting the power of the first RF signal prior to transmission to compensate for the first temperature and a third comparator circuit in communication with said second thermal reference device and said second RF signal power detector for adjusting the power of the second RF signal received at said second antenna to compensate for the second temperature.

5. A system as set forth in claim 1 further comprising a seventh comparator circuit in communication with said first comparator circuit and an altimeter for determining a concentration of nitrogen in the confined space based on at least the concentration of oxygen in the confined space and the altitude of the confined space.

6. A system as set forth in claim 1 wherein the second RF signal is in the 24 GHz frequency band.

7. A method of determining a concentration of a gas in a confined space, said method comprising the steps of:
generating a first radio frequency (RF) signal;
transmitting the first RF signal from a first antenna across the confined space;
detecting the power of the first RF signal prior to transmission through the confined space with a first RF signal power detector;
generating a first power signal corresponding to the first RF signal prior to transmission;
receiving the first RF signal at a second antenna;
detecting the power of the first RF signal received by the second antenna with a second RF signal power detector;
generating a second power signal corresponding to the first RF signal received by the second antenna;
sensing a temperature;
adjusting the first power signal and the second power signal to compensate for the temperature;
generating a second RF signal;
transmitting the second RF signal from a third antenna across the confined space;
receiving the second RF signal at a fourth antenna;
determining a concentration of water vapor in the confined space based on at least the second RF signal prior to transmission through the confined space and the second RF signal received by the fourth antenna; and
determining a concentration of oxygen in the confined space based on at least the first power signal and the second power signal and based on at least the power signals corresponding to the first RF signal and the concentration of water vapor in the confined space.

8. A method as set forth in claim 7 wherein said step of generating a first RF signal with a first frequency generator is further defined as generating a first RF signal having a frequency in the 60 GHz band with a first frequency generator.

9. A method as set forth in claim 7 wherein said step of sensing a temperature is further defined as sensing a first temperature adjacent the first RF signal power detector and sensing a second temperature adjacent the second RF signal power detector.

10. A method as set forth in claim 9 further comprising the step of adjusting the first power signal to compensate for the first temperature.

11. A method as set forth in claim 10 further comprising the step of adjusting the second power signal to compensate for the second temperature.

12. A method as set forth in claim 7 further comprising the step of determining a concentration of nitrogen in the confined space based on at least the concentration of oxygen in the confined space and the altitude of the confined space.

13. A system for determining a concentration of gas in a confined space, said system comprising:

a first frequency generator for generating a first radio frequency (RF) signal in the 60 GHz frequency band;
a first antenna electrically connected to said first frequency generator for transmitting the first RF signal across the confined space;
a second antenna for receiving the first RF signal;
a first RF signal power detector for detecting the power of the first RF signal prior to transmission through the confined space and generating a first power signal corresponding to the first RF signal prior to transmission;
a second RF signal power detector for detecting the power of the first RF signal received at said second antenna and generating a second power signal corresponding to the first RF signal received at said second antenna;
a first thermal reference device for sensing a first temperature;
a second thermal reference device for sensing a second temperature;
a second comparator circuit in communication with said first thermal reference device and said first RF signal power detector for adjusting the first power signal to compensate for the first temperature;
a third comparator circuit in communication with said second thermal reference device and said second RF signal power detector for adjusting the second power signal to compensate for the second temperature;
a first comparator circuit in communication with said first and second RF signal power detectors for determining a concentration of oxygen in the confined space based on the first power signal and the second power signal;
a second frequency generator for generating a second RF signal in the 24 GHz band;
a third antenna electrically connected to said second frequency generator for transmitting the second RF signal across the confined space;
a fourth antenna for receiving the RF signal; and
a sixth comparator circuit in communication with said second frequency generator and said fourth antenna for determining a concentration of water vapor in the confined space based on the second RF signal prior to transmission through the confined space and the second RF signal received by said fourth antenna,
wherein said first comparator circuit is in communication with said sixth comparator circuit for determining a concentration of water vapor in the confined space and determining a concentration of oxygen in the confined space based on the power signals corresponding to the first RF signal and the concentration of water vapor in the confined space and further comprising a seventh comparator circuit in communication with said first comparator circuit and an altimeter for determining a concentration of nitrogen in the confined space based on the concentration of oxygen in the confined space and the altitude of the confined space.

* * * * *